United States Patent [19]

Hodgen et al.

[11] Patent Number: 4,589,402

[45] Date of Patent: May 20, 1986

[54] METHOD OF IN VITRO FERTILIZATION

[75] Inventors: Gary D. Hodgen, Potomac, Md.; Howard W. Jones, Jr.; Georgeanna S. Jones, both of Norfolk, Va.

[73] Assignee: SErono Laboratories, Inc., Randolph, Mass.

[21] Appl. No.: 634,697

[22] Filed: Jul. 26, 1984

[51] Int. Cl.[4] ............................................. A61B 19/00
[52] U.S. Cl. .................................... 128/1 R; 424/100; 424/105; 604/55
[58] Field of Search ......................... 128/1 R; 604/55; 424/100, 105; 435/2

[56] References Cited

U.S. PATENT DOCUMENTS 3,854,470 12/1974 Augspurger ......................... 128/1 R
4,062,942 12/1977 Donini ................................. 424/100
4,339,434 7/1982 Ericsson ............................... 424/105

FOREIGN PATENT DOCUMENTS

WO82/00754 3/1982 PCT Int'l Appl. ...................... 1 R/

Primary Examiner—Dalton L. Truluck
Attorney, Agent, or Firm—Ostrolenk, Faber, Gerb & Soffen

[57] ABSTRACT

A method of in vitro fertilization therapy, which includes means for inducing ovulation by administering an exogenous human menopausal gonadotropin preparation and human chorionic gonadotropin, harvesting the mature follicles, combining the ovum with spermatazoa in vitro and transferring the conceptus into the uterus is improved by employing FSH as the exogenous human menopausal gonadotropin in the absence of exogenous LH.

3 Claims, 2 Drawing Figures

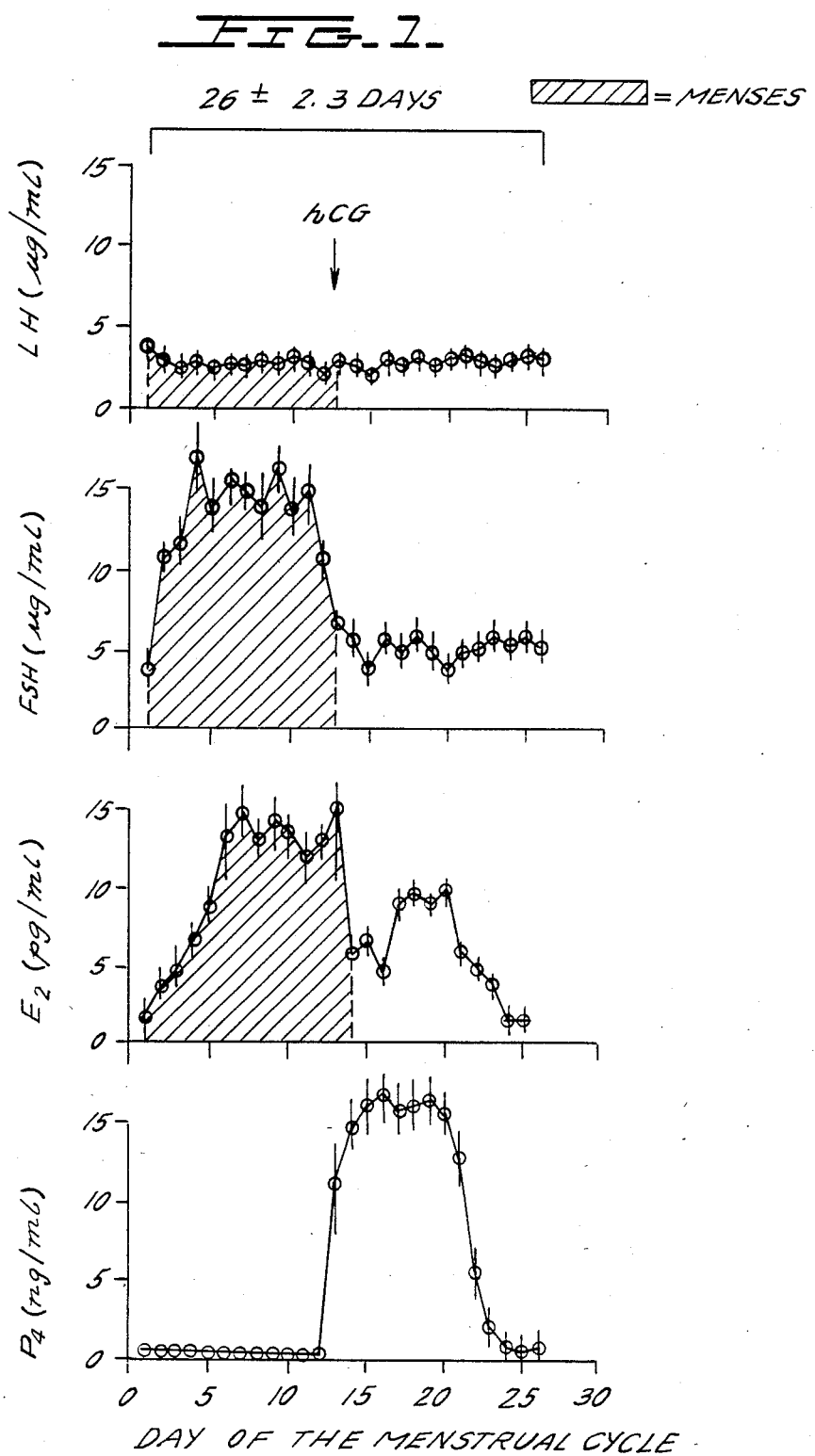

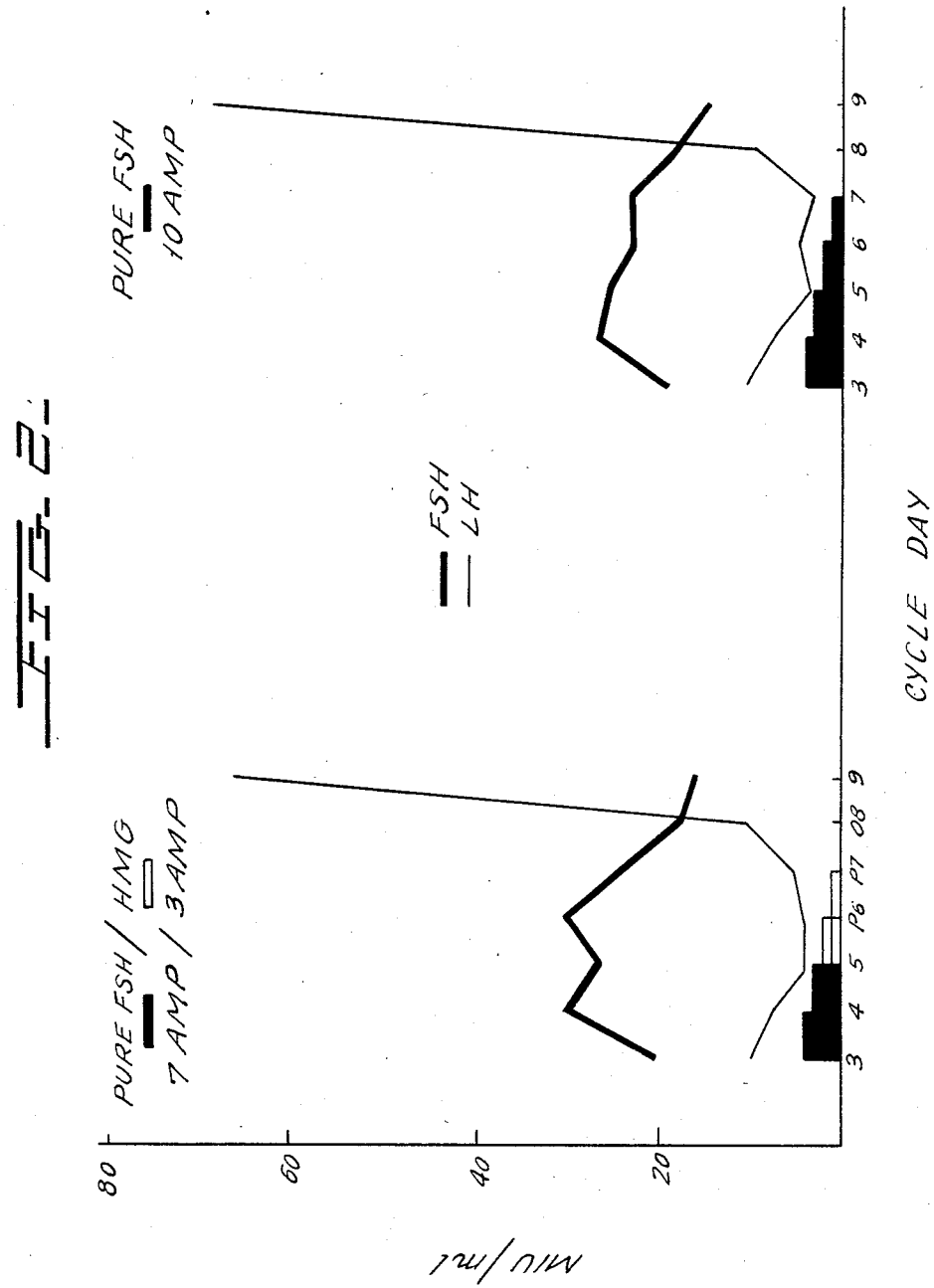

METHOD OF IN VITRO FERTILIZATION

BACKGROUND OF THE INVENTION

It is accepted dogma that typically ovulation of a single, fertilizable ovum each menstrual cycle completes a course of oogenesis that began during fetal development. It is not known, however, why from among the thousands of follicles present from birth, only a relative few are recruited each cycle to grow while at the same time others remain at rest. It is also not known why from the host of follicles maturing in each ovary, typically only a single follicle escapes atresia and is selected to ovulate each cycle. Since the vast majority of follicles fall victim to atresia (greater than 99%), understanding the selection of the follicle destined to ovulate is frought with the inherent difficulty of studying the rare exception rather than the predominant rule. One must be extremely careful to distinguish follicle growth that culminates in ovulation (gametogenic follicle growth) from that ending in atresia.

The latter stages of oogenesis in adults (i.e. folliculogenesis) are known to depend, to a large degree, on a complex interplay of hormones from the hypothalamus, pituitary and ovary. However, even though much more is understood about these endocrine relationships today, what determines the fate of an individual follicle remains largely unknown. Since in higher primates both ovaries are functional, the maturation of a single follicle with the potential to ovulate brings with it the obvious concomitant of one active and one quiescent (gametogenically) ovary each cycle. It is not known how just, typically, a single follicle matures to ovulation on only one ovary each cycle, even though both ovaries are perfused by a common systemic circulation.

Three glycoprotein hormones, luteinizing hormone (or LH), follicle stimulating hormone (or FSH) and human chorionic gonadotropin (or hCG) can act on the ovary to stimulate steroid synthesis and secretion. LH and FSH are secreted by the pituitary and together play a central role in regulating the ovarian menstrual cycle and ovulation. hCG is secreted by the developing placenta from the early stages of pregnancy and its role is to maintain steroid secretion by the corpus luteum, which is necessary to preserve the conceptus during early pregnancy.

In the normal or natural cycle, there is a midcycle surge in LH concentration in blood which is followed by ovulation. An elevated estrogen level, which is brought about by the endogenous secretion of LH and FSH acting to stimulate ovarian follicular maturation, is required for the LH surge to occur. The estrogen mediates a positive feedback mechanism which results in the increased LH secretion.

It is now known how to employ exogenous hormonal stimulation by administering mixed human menopausal gonadotropins, i.e. a combination of FSH and LH, as a prelude to ovulation or follicle aspiration for oocyte collection in in vitro fertilization techniques. Women and monkeys treated with such human menopausal gonadotropins often fail to demonstrate a timely LH surge despite serum estradiol levels ordinarily sufficient to elicit positive feedback for the LH surge. It has been concluded that the human menopausal gonadotropins stimulate the production of an ovarian factor or factors which blocks the pituitary LH response to estrogen as presented by Hodgen, Fert. Steril 38:281–380 and Schenkan and Hodgen J Clin Endocr Metab 57:50–55, 1983 and gonadotropin releasing hormone (GnRH). This blockage of GnRH action on the pituitary may be the mechanism by which the human menopausal gonadotropin stimulation prevents the estrogen mediated positive feedback of LH secretion. Non-human primates have been employed in research because of their extensive mimicry of many anatomic, functional and temporal characteristics of the hypothalamic-pituitary-ovarian-uterine axis in women. The individual variation in serum estrogen levels of endocrine normal individuals in response to human menopausal gonadotropin stimulation, as seen in these primates, is well recognized clinically also. This has resulted in the adoption of an individualized regimen for ovulation induction by human menopausal gonadotropin/hCG. Although LH surges do occur spontaneously, their appearance is sufficiently infrequent that hCG is routinely administered to induce ovulation.

Administration of human menopausal gonadotropins to ovulatory monkeys produces familiar bilateral ovarian hyperstimulation with attendant superphysiologic elevations of circulating estradiol. Despite these elevated estrogen levels, the monkeys usually failed to manifest timely gonadotropin responses to estrogen positive feedback, i.e., stereotypically these normal, intact, cycling primates do not have the expected midcycle like LH surges despite escalating levels of serum estradiol that usually exceed 400 pg/ml during 12 days of human menopausal gonadotropin therapy. An absence of spontaneous LH surges has also been observed when human menopausal gonadotropin induced ovarian hyperstimulation occurs in post-partum monkeys. These observations fit with the frequent clinical finding that when endocrinologically normal patients are given human menopausal gonadotropins to increase the number of follicles/ova available for in vitro fertilization and embryo transfer therapy, hCG is usually required for the final maturation of these follicles.

It is well established that the appropriate application of mixed exogenous gonadotropins has proved efficacious for ovulation induction or for multiple egg retrieval during in vitro fertilization therapy in women. Such in vitro fertilization therapy generally comprises the steps of inducing fertilization by administering exogeneous human menopausal gonadotropins, harvesting the ovulated follicles, combining the ovum with spermatozoa in vitro and transferring the conceptus into the uterus. However, ovarian stimulation through exogeneous gonadotropins for in vitro fertilization therapy is notoriously difficult to manage and the lack of uniform success with conventional human menopausal gonadotropin medications, those containing FSH and LH in nearly equal amounts, is widely appreciated. Individual responses to human menopausal gonadotropins vary markedly, thereby complicating patient management even when the most flexible (individualized) protocols are used as presented by Kenigsberg, Littman and Hodgen, Fert. & Steril. in press 1984.

It is the object of this invention to provide an improved method of inducing follicular maturation or ovulation by the administration of exogeneous FSH alone which increases the synchrony of follicular recruitment and selection during in vitro fertilization. As demonstrated in Schenken, Williams and Hodgen in Fert. & Steril. 41:629–634. This and other objects of the invention will become apparent to those skilled in the art from the following detailed description in which:

FIG. 1 shows the follicular ovulation brought about by hCG.

FIG. 2 graphs serum estradiol concentration as a function of the administration of a human FSH preparation lacking LH.

SUMMARY OF THE INVENTION

This invention relates to an improvement in in vitro fertilization involving the steps of inducing follicular maturation by administering exogeneous FSH harvesting oocytes the largest follicles, combining the ovum with spermatozoa in vitro and subsequent transfer of the conceptus into the uterus which is improved by employing FSH as the exogeneous human menopausal gonadotropin in the absence of exogeneous LH. The process of the invention is equally applicable to those individuals suffering from polycystic ovarian disease or other anovulatory disorders, i.e. those individuals who do not have normal intrinsic ovarian function and require ovulation induction to become pregnant through a regimen of "pure" FSH followed by hCG.

DESCRIPTION OF THE INVENTION

It has been found that the administration of exogeneous FSH in the absence of exogeneous LH is capable of inducing the development of multiple ovarian follicles which are responsive to hCG for in vitro fertilization therapy for ovulation.

LABORATORY PRIMATE STUDIES

Eleven adult female cynomolgus monkeys (Macaca fascicularis) were selected by Schenken and Hodgen (Fert. Steril. 41:629-634, 1984) for study based on records indicating regular menstrual cycles. The average body weight for these primates was 4.79±0.86 kg.

Counting the first day of spontaneous menses as cycle day 1, the monkeys were treated with 25 IU (im) of FSH twice daily according to three regimens. Group 1 received injections on cycle days 1-11; Group 2 on cycle days 1-4 and Group 3 on days 8-11. For all monkeys, laparoscopies were performed under ketamine anesthesia, beginning on the first day of FSH treatment and serially every 3 to 5 days thereafter to assess the status of ovarian follicular development. In order to test whether these FSH driven follicles could be ovulated, monkeys in Group 1 only received 1,000 IU (im) of hCG on day 12 and retrograde lavage of the fallopian tubes for egg collection 72 hours after hCG treatment was employed to determine whether ovulationn had actually occurred. Daily femoral blood samples were collected beginning on day 1 of the cycle and continued for 40 days or until menstruation. Sera were frozen until radioimmunoassay of LH, FSH, 17 β-estradiol and progesterone.

The injections of FSH on cycle days 1-11 induced dramatic and sustained elevations in serum FSH (about 15 ug/ml) and estradiol (about 500 pg/ml). Concurrently, ovarian hyperstimulation was manifested by obvious multiple follicular growth (10-15 prominent follicles by cycle day 8-11). Prior to hCG treatment, serum LH and progesterone remained at basal levels. Within 48 hours after hCG treatment, 1-3 ovulatory stigma were observed on each ovary. Mean serum progesterone and estradiol levels exceeded 15 ng/ml and 400 pg/ml, respectively, in mid-luteal phase, indicative of the collective secretory actions of multiple corpora lutea. That ovulation had actually occurred was indicated by the recovery of one or more eggs from the fallopian tubes of each female.

The monkeys treated with FSH during only the early follicular phase of the menstrual cycle demonstrated a prompt increase in serum FSH concentrations (mostly exogeneous) with mean levels near 15 ug/ml on day 4. On discontinuation of FSH injections, circulating FSH levels declined precipitously, below the limits of detection in radioimmunoassay (cycle days 8-11). Serum estradiol levels increased in parallel with the initial increase in circulating FSH, with mean peak values exceeding 300 pg/ml on cycle days 4-6 but even so, no LH surges were observed. Serum progesterone levels remained basal until the onset of the luteal phase in the subsequent spontaneous ovulatory cycle (day 24±2.4). Laparoscopy prior to FSH treatment revealed no advanced follicular development, while on cycle day 5, both ovaries were enlarged with multiple vesicular follicles. Following withdrawal of FSH treatment, the ovaries gradually returned to normal size over the subsequent week. No ovulatory stigma appeared.

Brief administration of FSH on cycle days 8-11 increased serum FSH levels similar to those found in Groups 1 and 2. Mean serum estradiol concentrations increased abruptly, but a spontaneous LH surge was present in only one of four monkeys. The follicular phase serum hormonal profiles for the solitary female were indistinguishable from those of an untreated ovulatory cycle.

The foregoing animal studies show that FSH can be administered alone to enhance the natural ovarian cycle.

INFERTILE PATIENT STUDIES

A patient who had received human menopausal gonadotropin stimulation for in vitro fertilization (cycle A) had conceptus transfers but had not become pregnant, agreed to an experimental protocol of pure FSH stimulation (cycle B). The individual was 35-40 years old and had a normal menstrual history. The stimulation in the initial cycle (cycle A) was as previously described in Garcia et al. "HMG/hCG Follicular Maturation for Oocyte Aspiration: Phase I", 1981 Fertil. Steril. 39:167 and Garcia et al. "HMG/hCG Follicular Maturation for Oocyte Aspiration: Phase II", 1981 Fertil. Steril. 39:174. The highest amount of gonadotropin was given during the first two days which were days 3 and 4 of a normal 28-day menstrual cycle and was decreased and discontinued as indicated in the aforementioned Garcia et al. articles. The patient had received supplementary FSH with the human menopausal gonadotropins during the first two days of the initial stimulation cycle. An effort was made to maintain the FSH dosages constant during cycle A and cycle B. Evaluation of follicular stimulation and maturation was made on the basis of daily serum estradiol ($E_2$) assays and the number of follicles developed for aspiration. Oocyte maturation was judged by the appearance of the oocyte, cumulus and corona radiata at aspiration. The normalcy of the oocyte was judged by fertilization and cleavage time and established by induction of pregnancy. The number of concepti transferred is used as a measure of the fertilization and cleavage time. The serum $E_2$ values were remarkably similar between cycles A and B during the first three or four days of stimulation, corresponding to cycle days 6 or 7. The individual had adequate FSH stimulation, as judged by the presence of a majority of preovulatory, rather than immature oocytes, and showed consistently increasing serum $E_2$ values in cycle B. The patient showed increased numbers of follicles, increased numbers of oocytes aspirated and increased numbers of concepti transferred. Pregnancy was successfully established.

Table I details the treatments and results.

TABLE I

Case 1 C.F.

| Cycle Day | Hrs. Post-Inj. | Cycle A FSH/LH | Cycle B FSH/LH | Cycle A $E_2$ | Cycle B $E_2$ |
|---|---|---|---|---|---|
| 3 | 0 | 300/150 | 300/— | 20 | 55 |
| 4 | 24 | 300/150 | 300/— | 103 | 101 |
| 5 | 48 | 150/150 | 150/— | 159 | 146 |
| 6 | 72 | 150/150 | 150/— | 176 | 243* |
| 7 | 96 | 150/150 | 150/— | 278 | 370* |
| 8 | 120 | hCG | — | 424 | 523* |
| 9 | | | hCG | (632) | 522 |
| 10 | 12 | | | | (771) |
| 11 | | | | | |
| Follicles | | #5 | 11 | | |
| Oocytes | | #5 | 10 | | |
| Preovulatory Oocytes | | #3 | 5 (2 Fractured Zona) | | |
| Immature Oocytes | | #2 | 4 | | |
| Atretic Oocytes | | 0 | 1 | | |
| Transfers | | 4 | 5 | | |
| Pregnancy | | − | + | | |

*Sig. difference from Cycle I
( )Value 16 hours post HCG

In the absence of additional LH, the FSH therapy in the normal woman was effective in maintaining an increased number of viable follicles. This is perhaps accomplished by preventing premature follicular atresia which is associated with an increase in post-mature oocytes. Greater numbers of viable oocytes are maintained as judged by (1) the morphologic appearance after laparoscopic retrieval, (2) ability to fertilize, cleave and (3) induce a pregnancy. It is interesting to note that both human menopausal gonadotropin and FSH stimulated cycles continued to show a spread of follicular maturation. Even with a large increase in the number of follicles stimulated and oocytes retrieved, the number of concepti transferred was similar. This may be indicative of an orderly progression of follicles into the "gonadotropin-responsive" maturation stage.

In in vitro fertilization therapy applied to ten women where gonadotropin stimulation was effected by FSH in the absence of LH, six became pregnant. This represents a drastic increase in the number of successful pregnancies, compared to therapy where the stimulation is by human menopausal gonadotropins, i.e. a combination of FSH and LH.

The same quantities of FSH can be employed as is employed in the conventional exogenous FSH/LH combinations. Generally, the amount of FSH administered daily to a woman being treated will be in the range of about 75–225 IU and preferably in the range of about 3–10 IU/kg/day. Intramuscular injection can be employed.

Various changes and modifications can be made in the process of this invention without departing from the spirit and scope thereof. The various embodiments which have been described herein were for the purpose of further illustrating the invention, but were not intended to limit it.

What is claimed is:

1. In a method of in vitro fertilization which comprises the initial steps of inducing follicular maturation by administering exogeneous human menopausal gonadotropins to a female, inducing ovulation, harvesting the eggs from large ovarian follicles, combining each ovum with spermatozoa in vitro and transferring the conceptus into the uterus, the improvement which consists of employing FSH alone as said exogenous human menopausal gonadotropin without the presence of exogeneous LH.

2. The method of claim 1, wherein the daily amount of FSH is about 5–10 IU/kg.

3. The method of claim 1, wherein an ovulatory inducing amount of hCG is administered.

* * * * *